United States Patent [19]

Schallner et al.

[11] Patent Number: 5,447,904
[45] Date of Patent: Sep. 5, 1995

[54] 3-ARYL-TRIAZINE-2,4-DIONES

[75] Inventors: Otto Schallner, Monheim; Klaus Lürssen, Bergisch Gladbach; Hans-Joachim Santel, Leverkusen; Robert R. Schmidt, Bergisch Gladbach; Renate Vosswinkel, Kürten-Bechen, all of Germany

[73] Assignee: Bayer Aktiengesellschaft, Leverkusen, Germany

[21] Appl. No.: 108,204

[22] Filed: Aug. 17, 1993

[30] Foreign Application Priority Data

Aug. 24, 1992 [DE] Germany .................. 42 28 000.1

[51] Int. Cl.⁶ .................. A01N 43/66; C07D 251/32; C07D 251/38; C07D 251/34
[52] U.S. Cl. .................. 504/227; 544/215; 544/220; 544/221; 544/222
[58] Field of Search .................. 504/227; 544/215, 220, 544/221, 222

[56] References Cited

U.S. PATENT DOCUMENTS 3,973,947  8/1976  Fuchs et al. .................. 71/93
3,989,501 11/1976  Kuratle, III .................. 504/227
4,839,359  6/1989  Führer et al. .................. 514/241

FOREIGN PATENT DOCUMENTS 1249516  1/1989  Canada .
0158075 10/1985  European Pat. Off. .
0201030 11/1986  European Pat. Off. .

*Primary Examiner*—Yogendra N. Gupta
*Attorney, Agent, or Firm*—Spring Horn Kramer & Woods

[57] ABSTRACT

The invention relates to new 3-aryl-triazine-2,4-diones of the general formula (I)

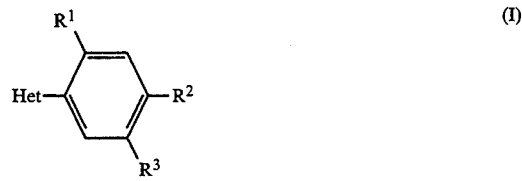

(I)

in which

Het represents a radical of the formula

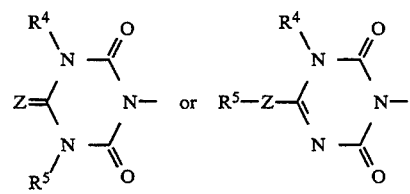

$R^1$ represents hydrogen or halogen,
$R^2$ represents halogen, cyano or nitro and
$R^3$ represents a radical of the formula $-X-R^6$ or $-CO-X-R^7$, in which
$R^4$ represents hydrogen, cyano, alkyl, alkenyl, alkinyl or halogenoalkyl,
$R^5$ represents alkyl, alkenyl or alkinyl,
$R^6$ represents hydrogen or optionally substituted alkyl,
$R^7$ represents hydrogen or optionally substituted alkyl,
X represents oxygen or sulphur and
Z represents oxygen or sulphur, to a process for their preparation, to new intermediates, and to their use as herbicides.

9 Claims, No Drawings

3-ARYL-TRIAZINE-2,4-DIONES

The invention relates to new 3-aryl-triazine-2,4-diones, to a process for their preparation, to new intermediates and to their use as herbicides.

It has been disclosed that certain triazine-2,4-diones such as, for example, the compound 3-isopropyl-6-[N-acetyl-N-(2,2-dimethyl-1-propyl)-amino]-(3H,5H)-1,3,5-triazine-2,4-dione have herbicidal properties (compare, for example, DE 2,603,180).

However, the herbicidal activity of these previously known compounds with respect to problem weeds as well as their compatibility with important crop plants is not entirely satisfactory in all fields of application.

New 3-aryl-triazine-2,4-diones have been found, of the general formula (I)

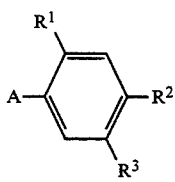

in which
A represents a radical of the formula

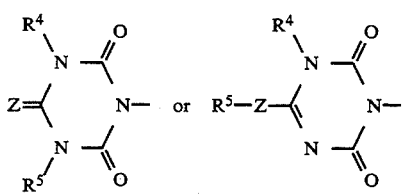

$R^1$ represents hydrogen or halogen,
$R^2$ represents halogen, cyano or nitro and
$R^3$ represents a radical of the formula —X—$R^6$ or —CO—X—$R^7$, in which
$R^4$ represents hydrogen, cyano, alkyl, alkenyl, alkinyl or halogenoalkyl,
$R^5$ represents alkyl, alkenyl or alkynyl,
$R^6$ represents hydrogen or optionally substituted alkyl,
$R^7$ represents hydrogen or optionally substituted alkyl,
X represents oxygen or sulphur and
Z represents oxygen or sulphur.

If appropriate, the compounds of the formula (I) can exist in the form of geometric and/or optical isomers or isomer mixtures of various composition, depending on the nature of the substituents. The invention claims the pure isomers as well as the isomer mixtures.

Furthermore, it has been found that the new 3-aryl-triazine-2,4-diones of the general formula (I)

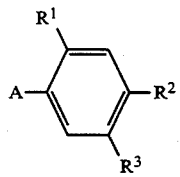

in which
A represents a radical of the formula

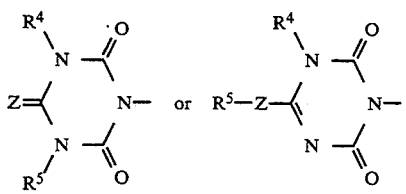

$R^1$ represents hydrogen or halogen,
$R^2$ represents halogen, cyano or nitro and
$R^3$ represents a radical of the formula —X—$R^6$ or —CO—X—$R^7$, in which
$R^4$ represents hydrogen, cyano, alkyl, alkenyl, alkynyl or halogenoalkyl,
$R^5$ represents alkyl, alkenyl or alkynyl,
$R^6$ represents hydrogen or optionally substituted alkyl,
$R^7$ represents hydrogen or optionally substituted alkyl,
X represents oxygen or sulphur and
Z represents oxygen or sulphur,
are obtained when substituted phenylurea derivatives of the general formula (II)

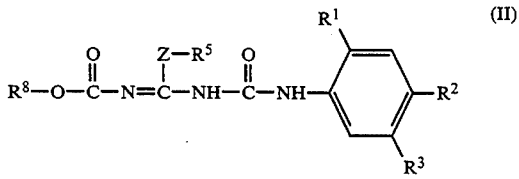

in which
$R^1$, $R^2$, $R^3$, $R^5$ and Z have the abovementioned meanings and
$R^8$ represents alkyl or aryl,
are cyclised if appropriate in the presence of a diluent and if appropriate in the presence of a reaction auxiliary and, if appropriate, the resulting 3-aryl-(1H)-triazine-2,4-diones of the formula (Ia)

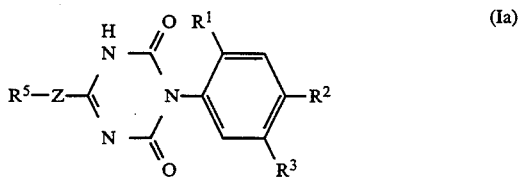

in which
$R^1$, $R^2$, $R^3$, $R^5$ and Z have the the abovementioned meanings
are reacted in a subsequent 2nd step with alkylating agents of the formula (III),

$R^{4-1}$—E (III)

in which
$R^{4-1}$ represents alkyl, alkenyl, alkinyl or halogenoalkyl and
E represents an electron-attracting leaving group,
or with cyanogen bromide, if appropriate in the presence of a diluent and if appropriate in the presence of a reaction auxiliary, and, if appropriate, the resulting 3-aryl-triazine-2,4-diones of the formula (Ib)

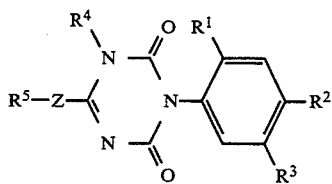

in which
R$^1$, R$^2$, R$^3$, R$^4$, R$^5$ and Z have the the abovementioned meanings
are subjected in a subsequent 3rd step to thermal isomerisation, if appropriate in the presence of a diluent and if appropriate in the presence of a reaction auxiliary.

Finally, it has been found that the new 3-aryl-triazine-2,4-diones of the general formula (I) have herbicidal properties.

Surprisingly, the 3-aryl-triazine-2,4-diones of the general formula (I) have a considerably better herbicidal activity against problem weeds combined with a considerably better compatibility with important crop plants in comparison with the triazine-2,4-diones which are known from the prior art, such as, for example, the compound 3-isopropyl-6[N-acetyl-N-(2,2-dimethyl-1-propyl)-amino]-(3H,5H)-1,3,5-triazine-2,4-dione, which are similar compounds chemically and from a point of view of their action.

Formula (I) provides a general definition of the 3-aryl-triazine-2,4-diones according to the invention. Preferred compounds of the formula (I) are those in which
A represents a radical of the formula

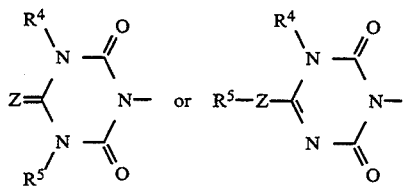

R$^1$ represents hydrogen, fluorine, chlorine bromine or iodine,

R$^2$ represents fluorine, chorine bromine, iodine, cyano or nitro,

R$^3$ represents a radical of the formula —X—R$^6$ or —CO—X—R$^7$ in which

R$^4$ represents hydrogen, cyano, straight-chain or branched alkyl having 1 to 8 carbon atoms, straight-chain or branched alkenyl having 2 to 8 carbon atoms, straight-chain or branched alkynyl having 2 to 8 carbon atoms or straight-chain or branched halogenoalkyl having 1 to 6 carbon atoms and 1 to 13 identical or different halogen atoms, in particular fluorine, chlorine, bromine and/or iodine, R$^5$ represents straight-chain or branched alkyl having 1 to 8 carbon atoms, straight-chain or branched alkenyl having 2 to 8 carbon atoms or straight-chain or branched alkinyl having 2 to 8 carbon atoms, R$^6$ represents hydrogen, straight-chain or branched alkyl having 1 to 8 carbon atoms, straight-chain or branched halogenoalkyl having 1 to 6 carbon atoms and 1 to 13 identical or different halogen atoms, in particular fluorine, chlorine, bromine and/or iodine, or represents in each case straight-chain or branched alkoxyalkyl, alkoxycarbonylalkyl, alkylcarbonyloxyalkyl, alkylthiocarbonylalkyl or alkylcarbonylthioalkyl, each of which has 1 to 6 carbon atoms in the individual alkyl moieties, or represents arylalkyl which has 6 or 10 carbon atoms in the aryl moiety and 1 to 6 carbon atoms in the straight-chain or branched alkyl moiety and which is optionally monosubstituted or polysubstituted by identical or different substituents, suitable aryl substituents being:

halogen, cyano, nitro, in each case straight-chain or branched alkyl, alkoxy, alkylthio, alkylsulphinyl or alkylsulphonyl, each of which has 1 to 4 carbon atoms, in each case straight-chain or branched halogenoalkyl, halogenoalkoxy, halogenoalkylthio, halogenoalkylsulphinyl or halogenoalkylsulphonyl, each of which has 1 to 4carbon atoms and 1 to 9 identical or different halogen atoms, in each case straight-chain or branched alkoxycarbonyl or alkoximinoalkyl, each of which has 1 to 4 carbon atoms in the individual alkyl moieties, or phenyl which is optionally monosubstituted or polysubstituted by identical or different substituents from the series comprising halogen and/or straight-chain or branched alkyl and/or straight-chain or branched alkoxy and/or straight-chain or branched halogenoalkyl and/or straight-chain or branched halogenoalkoxy, each of which has 1 to 4 carbon atoms and, if appropriate, 1 to 9 identical or different halogen atoms, R$^7$ represents hydrogen, straight-chain or branched alkyl having 1 to 8 carbon atoms, straight-chain or branched halogenoalkyl having 1 to 6 carbon atoms and 1 to 13 identical or different halogen atoms, in particular fluorine, chlorine, bromine and/or iodine, in each case straight-chain or branched alkoxyalkyl, alkoxycarbonylalkyl, alkylcarbonyloxyalkyl, alkylthiocarbonylalkyl or alkylcarbonylthioalkyl, each of which has 1 to 6 carbon atoms in the individual alkyl moieties or represents arylalkyl which has 6 or 10 carbon atoms in the aryl moiety and 1 to 6 carbon atoms in the straight-chain or branched alkyl moiety and which is optionally monosubstituted or polysubstituted by identical or different substituents, suitable aryl substituents being:

halogen, cyano, nitro, in each case straight-chain or branched alkyl, alkoxy, alkylthio, alkylsulphinyl or alkylsulphonyl, each of which has 1 to 4 carbon atoms, in each case straight-chain or branched halogenoalkyl, halogenoalkoxy, halogenoalkylthio, halogenoalkylsulphinyl or halogenoalkylsulphonyl, each of which has 1 to 4 carbon atoms and 1 to 9 identical or different halogen atoms, in each case straight-chain or branched alkoxycarbonyl or alkoximinoalkyl, each of which has 1 to 4 carbon atoms in the individual alkyl moieties, or phenyl which is optionally monosubstituted or polysubstituted by identical or different substituents from the series comprising halogen and/or straight-chain or branched alkyl and/or straight-chain or branched alkoxy and/or straight-chain or branched halogenoalkyl and/or straight-chain or branched halogenoalkoxy, each of which has 1 to 4 carbon atoms and, if appropriate, 1 to 9 identical or different halogen atoms, X represents oxygen or sulphur and Z represents oxygen or sulphur.

Particularly preferred compounds of the formula (I) are those in which

A represents a radical of the formula

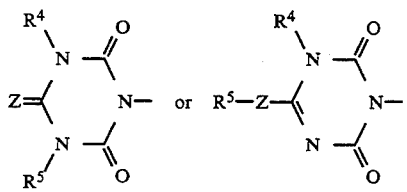

R¹ represents hydrogen, fluorine, chlorine or bromine,

R² represents fluorine, chlorine, bromine, cyano or nitro,

R³ represents a radical of the formula —X—R⁶ or —CO—X—R⁷, in which

R⁴ represents hydrogen, cyano, straight-chain or branched alkyl having 1 to 6 carbon atoms, straight-chain or branched alkenyl having 2 to 6 carbon atoms, straight-chain or branched alkynyl having 2 to 6 carbon atoms or straight-chain or branched halogenoalkyl having 1 to 4 carbon atoms and 1 to 9 identical or different halogen atoms, in particular fluorine, chlorine and/or bromine, R⁵ represents straight-chain or branched alkyl having 1 to 6 carbon atoms, straight-chain or branched alkenyl having 2 to 6 carbon atoms or straight-chain or branched alkynyl having 2 to 6 carbon atoms, R⁶ represents hydrogen, straight-chain or branched alkyl having 1 to 6 carbon atoms, straight-chain or branched halogenoalkyl having 1 to 4 carbon atoms and 1 to 9 identical or different halogen atoms, in particular fluorine, chlorine and/or bromine, or represents in each case straight-chain or branched alkoxyalkyl, alkoxycarbonylalkyl, alkylcarbonyloxyalkyl, alkylthiocarbonylalkyl or alkylcarbonylthioalkyl, each of which has 1 to 4 carbon atoms in the individual alkyl moieties, or represents phenylalkyl which has 1 to 4 carbon atoms in the straight-chain or branched alkyl moiety and which is optionally monosubstituted to pentasubstituted by identical or different substituents, suitable phenyl substituents being:

halogen, cyano, nitro, in each case straight-chain or branched alkyl, alkoxy, alkylthio, alkylsulphinyl or alkylsulphonyl, each of which has 1 to 3 carbon atoms, in each case straight-chain or branched halogenoalkyl, halogenoalkoxy, halogenoalkylthio, halogenoalkylsulphinyl or halogenoalkylsulphonyl, each of which has 1 to 3 carbon atoms and 1 to 7 identical or different halogen atoms, in each case straight-chain or branched alkoxycarbonyl or alkoximinoalkyl, each of which has 1 to 3 carbon atoms in the individual alkyl moieties, or phenyl which is optionally monosubstituted or polysubstituted by identical or different substituents from the series comprising halogen and/or straight-chain or branched alkyl and/or straight-chain or branched alkoxy and/or straight-chain or branched halogenoalkyl and/or straight-chain or branched halogenoalkoxy, each of which has 1 to 3 carbon atoms and, if appropriate, 1 to 7 identical or different halogen atoms, R⁷ represents hydrogen, straight-chain or branched alkyl having 1 to 6 carbon atoms, straight-chain or branched halogenoalkyl having 1 to 4 carbon atoms and 1 to 9 identical or different halogen atoms, in particular fluorine, chlorine and/or bromine, or represents in each case straight-chain or branched alkoxyalkyl, alkoxycarbonylalkyl, alkylcarbonyloxyalkyl, alkylthiocarbonylalkyl or alkylcarbonylthioalkyl, each of which has 1 to 4 carbon atoms in the individual alkyl moieties, or represents phenylalkyl which has 1 to 4 carbon atoms in the straight-chain or branched alkyl moiety and which is optionally monosubstituted to pentasubstituted by identical or different substituents, suitable phenyl substituents being:

halogen, cyano, nitro, in each case straight-chain or branched alkyl, alkoxy, alkylthio, alkylsulphinyl or alkylsulphonyl, each of which has 1 to 3 carbon atoms, in each case straight-chain or branched halogenoalkyl, halogenoalkoxy, halogenoalkylthio, halogenoalkylsulphinyl or halogenoalkylsulphonyl, each of which has 1 to 3 carbon atoms and 1 to 7 identical or different halogen atoms, in each case straight-chain or branched alkoxycarbonyl or alkoximinoalkyl, each of which has 1 to 3 carbon atoms in the individual alkyl moieties, or phenyl which is optionally monosubstituted or polysubstituted by identical or different substituents from the series comprising halogen and/or straight-chain or branched alkyl and/or straight-chain or branched alkoxy and/or straight-chain or branched halogenoalkyl and/or straight-chain or branched halogenoalkoxy, each of which has 1 to 3 carbon atoms and, if appropriate, 1 to 7 identical or different halogen atoms, X represents oxygen or sulphur and Z represents oxygen or sulphur.

Very particularly preferred compounds of the formula (I) are those in which

A represents a radical of the formula

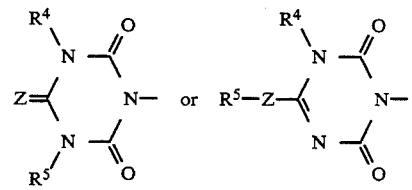

R¹ represents hydrogen, fluorine or chlorine,

R² represents fluorine, chlorine, cyano or nitro,

R³ represents a radical of the formula —X—R⁶ or —CO—X—R⁷, in which

R⁴ represents hydrogen, cyano, straight-chain or branched alkyl having 1 to 4 carbon atoms, straight-chain or branched alkenyl having 2 to 4 carbon atoms, straight-chain or branched alkynyl having 2 to 4 carbon atoms or straight-chain or branched halogenoalkyl having 1 to 3 carbon atoms and 1 to 7 identical or different halogen atoms, in particular fluorine, chlorine and/or bromine, R[5] represents straight-chain or branched alkyl having 1 to 4 carbon atoms, straight-chain or branched alkenyl having 2 to 4 carbon atoms or straight-chain or branched alkynyl having 2 to 4 carbon atoms, R[6] represents hydrogen, straight-chain or branched alkyl having 1 to 4 carbon atoms, straight-chain or branched halogenoalkyl having 1 to 3 carbon atoms and 1 to 7 identical or different halogen atoms, in particular fluorine, chlorine or bromine, or represents in each case straight-chain or branched alkoxyalkyl, alkoxycarbonylalkyl, alkylcarbonyloxyalkyl, alkylthiocarbonylalkyl or alkylcarbonylthioalkyl, each of which has 1 to 3 carbon atoms in the individual alkyl moieties, or represents phenylalkyl which has 1 to 2 carbon atoms in the alkyl moiety and which is optionally monosubstituted to trisubstituted by identical or different substituents, suitable phenyl substituents being:

fluorine, chlorine, bromine, cyano, nitro, methyl, ethyl, n- or i-propyl, n-, i-, s- or t-butyl, methoxy, ethoxy, n- or i-propoxy, n-, i-, s- or t-butoxy, methylthio, ethylthio, methylsulphinyl, ethylsulphinyl, methylsulphonyl, ethylsulphonyl, trifluoromethyl, difluoromethyl, trifluoromethoxy, difluoromethoxy, trifluoromethylthio, trifluoromethylsulphinyl, trifluoromethylsulphonyl, methoxycarbonyl, ethoxycarbonyl, methoximinomethyl, methoximinoethyl, ethoximinomethyl, ethoximinoethyl, or phenyl which is optionally monosubstituted to trisubstituted by identical or different substituents from the series comprising fluorine, chlorine, bromine, methyl, ethyl, n- or i-propyl, methoxy, ethoxy, trifluoromethyl and/or trifluoromethoxy, 'R[7] represents hydrogen, straight-chain or branched alkyl having 1 to 4 carbon atoms, straight-chain or branched halogenoalkyl having 1 to 3 carbon atoms and 1 to 7 identical or different halogen atoms, in particular fluorine, chlorine or bromine, or represents in each case straight-chain or branched alkoxyalkyl, alkoxycarbonylalkyl, alkylcarbonyloxyalkyl, alkylthiocarbonylalkyl or alkylcarbonylthioalkyl, each of which has 1 to 3 carbon atoms in the individual alkyl moieties, or represents phenylalkyl which has 1 to 2 carbon atoms in the alkyl moiety and which is optionally monosubstituted to trisubstituted by identical or different substituents, suitable phenyl substituents being:

fluorine, chlorine, bromine, cyano, nitro, methyl, ethyl, n- or i-propyl, n-, i-, s- or t-butyl, methoxy, ethoxy, n- or i-propoxy, n-, i-, s- or t-butoxy, methylthio, ethylthio, methylsulphinyl, ethylsulphinyl, methylsulphonyl, ethylsulphonyl, trifluoromethyl, difluoromethyl, trifluoromethoxy, difluoromethoxy, trifluoromethylthio, trifluoromethylsulphinyl, trifluoromethylsulphonyl, methoxycarbonyl, ethoxycarbonyl, methoximinomethyl, methoximinoethyl, ethoximinomethyl, ethoximinoethyl, or phenyl which is optionally monosubstituted to trisubstituted by identical or different substituents from the series comprising fluorine, chlorine, bromine, methyl, ethyl, n- or i-propyl, methoxy, ethoxy, trifluoromethyl and/or trifluoromethoxy, X represents oxygen or sulphur and
Z represents oxygen or sulphur.

Reference may be made specifically the compounds mentioned in the preparation examples.

If, for example, N-(4-chloro-2-fluoro-5-methoxycarbonyl-phenyl)-N'-(1-ethoxy-1-methoxycarbonyliminomethyl)-urea is used as starting compound and methyl iodide as the alkylating agent, the course of the reaction of the process according to the invention can be represented by the following equation:

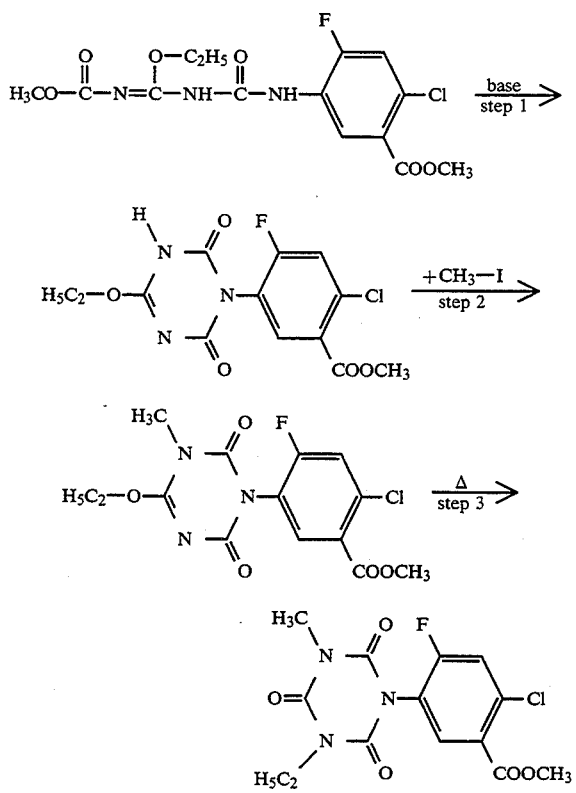

Formula (II) provides a general definition of the substituted phenylurea derivatives required as starting materials for carrying out the process according to the invention. In this formula (II), R[1], R[2], R[3], R[5] and Z preferably represent those radicals which have already been mentioned in connection with the description of the compounds of the formula (I) according to the invention as being preferred for these substituents. R[8] preferably represents straight-chain or branched alkyl having 1 to 6 carbon atoms or phenyl, in particular methyl or ethyl or phenyl.

The substituted phenylurea derivatives of the formula (II) were hitherto unknown and are also subject of the invention. They are obtained when phenyl isocyanates of the formula (IV)

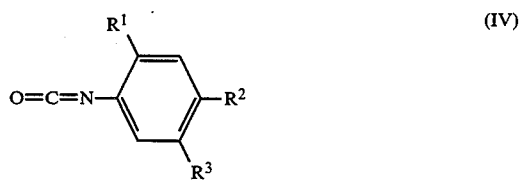

in which
R[1], R[2] and R[3] have the abovementioned meanings, are reacted with carbamic acid derivatives of the formula (V),

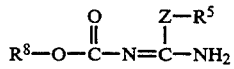

$$\begin{matrix} & O & Z-R^5 \\ & \| & | \\ R^8-O-C-N=C-NH_2 \end{matrix} \quad (V)$$

in which $R^5$, $R^8$ and Z have the abovementioned meanings, at temperatures between 0° C. and 50° C., if appropriate in the presence of a diluent such as, for example, dichloromethane. It is also possible to prepare the phenyl isocyanates of the formula (IV) which are required as starting compounds in a preceding reaction in the generally customary manner starting from suitable anilines and phosgene or diphosgene and to react them further with the carbamic acid derivatives of the formula (V) without isolation directly in the reaction vessel (compare, in this context, also the preparation examples).

The phenyl isocyanates of the formula (IV) are generally known compounds of organic chemistry or can be obtained in analogy to generally known processes (compare, for example, GB 1,435,585).

The carbamic acid derivatives of the formula (V) are also generally known compounds of organic chemistry (compare, for example, DE 2,933,889; Liebigs Ann. Chem. 1985, 2363–2370).

Formula (III) provides a general definition of the alkylating agents furthermore required as starting materials for carrying out the process according to the invention. In this formula (III), $R^{4-1}$ preferably represents straight-chain or branched alkyl having 1 to 6 carbon atoms, straight-chain or branched alkenyl having 2 to 6 carbon atoms, straight-chain or branched alknyl having 2 to 6 carbon atoms or straight-chain or branched halogenoalkyl having 1 to 6 carbon atoms and 1 to 13 identical or different halogen atoms, in particular fluorine, chlorine, bromine and/or iodine. $R^{4-1}$ represents, in particular, straight-chain or branched alkyl having 1 to 4 carbon atoms, straight-chain or branched alkenyl having 2 to 4 carbon atoms, straight-chain or branched alkynyl having 2 to 4 carbon atoms or straight-chain or branched halogenoalkyl having 1 to 4 carbon atoms and 1 to 9 identical or different halogen atoms, in particular fluorine, chlorine and/or bromine.

E represents a leaving radical which is customary in alkylating agents, preferably halogen, in particular chlorine, bromine or iodine, or represents in each case optionally substituted alkylsulphonyloxy, alkoxysulphonyloxy or arylsulphonyloxy such as, in particular, methanesulphonyloxy, trifluoromethanesulphonyloxy, methoxysulphonyloxy, ethoxysulphonyloxy or p-toluenesulphonyloxy.

The alkylating agents of the formula (III) are also generally known compounds of organic chemistry.

Suitable diluents for carrying out step 1 of the process according to the invention are all customary organic or inorganic solvents. These include, in particular, aliphatic, alicyclic or aromatic, optionally halogenated hydrocarbons such as, for example, benzine, benzene, toluene, xylene, chlorobenzene, dichlorobenzene, petroleumether, hexane, cyclohexane, dichloromethane, chloroform, carbon tetrachloride; ethers, such as diethyl ether, diisopropyl ether, dioxane, tetrahydrofuran or ethylene glycol dimethyl ether or ethylene glycol diethyl ether; ketones such as acetone, butanone or methyl isobutyl ketone; nitriles such as acetonitrile, propionitrile or benzonitrile; amides such as N,N-dimethylformamide, N,N-dimethylacetamide, N-methylformanilide, N-methylpyrrolidone or hexamethylphosphoric triamide; esters such as methyl acetate or ethyl acetate; sulphoxides, such as dimethyl sulphoxide or alcohols, such as methanol, ethanol, propanol or butanol.

If appropriate, step 1 of the process according to the invention can be carried out in the presence of a suitable basic reaction auxiliary. Suitable for this purpose are all customary inorganic or organic bases. These include, for example, alkaline earth metal hydroxides, alkali metal hydroxides, such as sodium hydroxide, calcium hydroxide, potassium hydroxide or else ammonium hydroxide, alkali metal carbonates, such as sodium carbonate, potassium carbonate, potassium hydrogen carbonate, sodium hydrogen carbonate or ammonium carbonate, alkali metal acetates or alkaline earth metal acetates, such as sodium acetate, potassium acetate, calcium acetate or ammonium acetate, as well as tertiary amines such as trimethylamine, triethylamine, tributylamine, N,N-dimethylaniline, pyridine, N-methylpiperidine, N,N-dimethylaminopyridine, diazabicyclooctane (DABCO), diazabicyclonene (DBN) or diazabicycloundecene (DBU).

When carrying out step 1 of the process according to the invention, the reaction temperatures can be varied within a substantial range. In general, step 1 of the process according to the invention is carried out at temperatures between 0° C. and 120° C., preferably at temperatures between 20° C. and 80° C.

Step 1 of the process according to the invention is customarily carried out under atmospheric pressure. However, it can also be carried out under increased or reduced pressure.

For carrying out step 1 of the process according to the invention, 0.01 to 2.0 mol, preferably 0.1 to 1.0 mol, of base are generally employed as reaction auxiliary per mole of substituted phenylurea derivative of the formula (II). The reaction is carried out and the reaction products are worked up and isolated in analogy to known processes (compare, in this context, also the preparation examples).

Suitable diluents for carrying out step 2 of the process according to the invention are inert organic solvents. These include, in particular, aliphatic, alicyclic or aromatic, optionally halogenated hydrocarbons such as, for example, benzine, benzene, toluene, xylene, chlorobenzene, dichlorobenzene, petroleum ether, hexane, cyclohexane, dichloromethane, chloroform, carbon tetrachloride; ethers such as diethyl ether, diisopropyl ether, dioxane, tetrahydrofuran or ethylene glycol dimethyl ether or ethylene glycol diethyl ether; ketones such as acetone, butanone or methyl isobutyl ketone; nitriles such as acetonitrile, propionitrile or benzonitrile; amides such as N,N-dimethylformamide, N,N-dimethylacetamide, N-methylformanilide, N-methylpyrrolidone or hexamethylphosphoric triamide; esters such as methyl acetate or ethyl acetate, or sulphoxides such as dimethyl sulphoxide.

Step 2 of the process according to the invention is preferably carried out in the presence of a suitable reaction auxiliary. Suitable reaction auxiliaries are all customary inorganic or organic bases. These include, for example, the hydrides, hydroxides, amides, alcoholates, acetates, carbonates or hydrogen carbonates of alkaline earth metals or alkali metals such as, for example, sodium hydride, sodium amide, sodium methylate, sodium ethylate, potassium tert.-butylate, sodium hydroxide, potassium hydroxide, ammonium hydroxide, sodium acetate, potassium acetate, calcium acetate, ammonium acetate, sodium carbonate, potassium carbonate, potassium hydrogen carbonate, sodium hydrogen carbonate or ammonium carbonate as well as tertiary amines such as trimethylamine, triethylamine, tributylamine, N,N-dimethylaniline, pyridine, N-methylpiperidine, N,N-dimethylaminopyridine, diazabicyclooctane (DABCO), diazabicyclononene (DBN) or diazabicycloundecene (DBU).

If appropriate, step 2 of the process according to the invention can also be carried out in a two-phase system such as, for example, water/toluene or water/dichloromethane, if appropriate in the presence of a suitable phase transfer catalyst. Examples of such catalysts which may be mentioned are: tetrabutylammonium iodide, tetrabutylammonium bromide, tetrabutylammonium chloride, tributyl-methylphosphonium bromide, trimethyl-$C_{13}$/$C_{15}$-alkylammonium chloride, trimethyl-$C_{13}$/$C_{15}$-alkylammonium bromide, dibenzyl-dimethyl-ammonium methylsulphate, dimethyl-$C_{12}$/$C_{14}$-alkyl-benzylammonium chloride, dimethyl-$C_{12}$/$C_{14}$-alkyl-benzylammonium bromide, tetrabutylammonium-hydroxide triethylbenzylammonium chloride, methyltrioctylammonium chloride, trimethyl-benzylammonium chloride, 15-crown-5, 18-crown-6 or tri-[2-(2-methoxyethoxy)-ethyl]-amine.

When carrying out step 2 of the process according to the invention, the reaction temperatures can be varied within a substantial range. In general, step 2 of the process according to the invention is carried out at temperatures between −20° C. and +120° C., preferably at temperatures between 0° C. and 80° C.

Step 2 of the process according to the invention is customarily carried out under atmospheric pressure. However, it can also be carried out under increased or reduced pressure.

For carrying out step 2 of the process according to the invention, 1.0 to 5.0 mol, preferably 1.0 to 2.5 mol, of alkylating agent of the formula (III) or alternatively cyanogen bromide, 1.0 to 5.0 mol, preferably 1.0 to 2.5 mol, of base as reaction auxiliary and, if appropriate, 0,001 to 2.0 mol, preferably 0.001 to 1.0 mol, of the phase transfer catalyst are generally employed per mole of 3-aryl-(1H)-triazine-2,4-dione of the formula (Ia).

The reaction is carried out and the reaction products are worked up and isolated in analogy to known processes (compare, in this context, also the preparation examples).

Suitable diluents for carrying out step 3 of the process according to the invention are customary inert organic solvents. These include, in particular, aliphatic, alicyclic or aromatic, optionally halogenated hydrocarbons such as, for example, benzine, benzene, toluene, xylene, chlorobenzene, dichlorobenzene, petroleum ether, hexane, cyclohexane, dichloromethane, chloroform, carbon tetrachloride; ethers such as diethyl ether, diisopropyl ether, dioxane, tetrahydrofuran or ethylene glycol dimethyl ether or ethylene glycol diethyl ether; ketones such as acetone, butanone or methyl isobutyl ketone; nitriles such as acetonitrile, propionitrile or benzonitrile; amides, such as N,N-dimethylformamide, N,N dimethylacetamide, N-methylformanilide, N-methylpyrrolidone or hexamethylphosphoric triamide; esters such as methyl acetate or ethyl acetate, or sulphoxides such as dimethyl sulphoxide.

If appropriate, step 3 of the process according to the invention can also be carried out in the presence of a suitable basic reaction auxiliary. Suitable basic reaction auxiliaries are all customary inorganic or organic bases. These include, for example, alkaline earth metal hydroxides or alkali metal hydroxides such as sodium hydroxide, calcium hydroxide, potassium hydroxide or else ammonium hydroxide, alkali metal carbonates such as sodium carbonate, potassium carbonate, potassium hydrogen carbonate, sodium hydrogen carbonate or ammonium carbonate, alkali metal acetates or alkaline earth metal acetates, such as sodium acetate, potassium acetate, calcium acetate or ammonium acetate, as well as tertiary amines such as trimethylamine, triethylamine, tributylamine, N,N-dimethylaniline, pyridine, N-methylpiperidine, N,N-dimethylaminopyridine, diazabicyclooctane (DABCO), diazabicyclonones (DBN) or diazabicycloundecene (DBU).

When carrying out step 3 of the process according to the invention, the reaction temperatures can be varied within a substantial range. In general, step 3 of the process according to the invention is carried out at temperatures between 50° C. and 200° C., preferably at temperatures between 80° C. and 150° C.

Step 3 of the process according to the invention is customarily carried out under atmospheric pressure. However, it can also be carried out under increased or reduced pressure.

For carrying out step 3 of the process according to the invention, 0.01 to 2.0 mol, preferably 0.1 to 1.0 mol, of base are generally employed as reaction auxiliary per mole of substituted 3-aryl-triazine-2,4-dione of the formula (Ib), however, it is also possible to carry out step 3 of the process according to the invention without the addition of a basic reaction auxiliary. The reaction is carried out and the reaction products are worked up and isolated in analogy to known processes (compare, in this context, also the preparation examples).

The end products of the formula (I) are purified with the aid of customary processes, for example by column chromatography or by recrystallisation.

They are characterised with the aid of the melting point or, in the case of compounds which do not form crystals, with the aid of refractive index or proton nuclear resonance spectroscopy ($^1$H NMR).

The active compounds according to the invention can be used as defoliants, desiccants, agents for destroying broad-leaved plants and, especially, as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, portulaca, Xanthium, Convolvulus, Ipomoea, polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledon cultures of the genera: Gossypium, Glycine, Beta, Daucus, phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, panicum, Saccharum, Ananas, Asparagus and Allium. However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, on lawns, turf and pasture-land, and for the selective combating of weeds in annual cultures.

In this context, the active compounds according to the invention can be employed with particularly good success for combating monocotyledon and dicotyledon weeds in monocotyledon and dicotyledon cultures such as, for example, maize, wheat, sugar beet and soya beans.

In addition, the active compounds according to the invention also engage in the metabolism of the plants and can therefore be employed as growth regulators.

Experience to date of the mode of action of plant growth regulators has shown that an active compound can also exert several different actions on plants. The actions of the compounds depend essentially on the point in time at which they are used, relative to the stage of development of the plant, and on the amounts of active compound applied to the plants or their environment and on the way in which the compounds are applied. In each case, growth regulators are intended to influence the crop plants in the particular manner desired.

The amount of leaf on plants can be controlled, under the influence of growth regulators, so that defoliation of the plants at a desired point in time is achieved. Such defoliation is of great importance in the mechanical harvesting of cotton, but is also of interest for facilitating harvesting in other cultures, such as, for example, in viticulture. Defoliation of the plants can also be carried out to lower the transpiration of plants before they are transplanted.

In addition, the active compounds according to the invention also have fungicidal activity when applied in suitable amounts and they can be employed, inter alia, for combating rice diseases such as, for example, against the organism of rice blast disease (Pyricularia oryzae).

The active compounds can be converted into the customary formulations, such as solutions, emulsions, suspensions, powders, foams, pastes, granules, aerosols, natural and synthetic materials impregnated with active compound, and very fine capsules in polymeric substances.

These formulations are produced in a known manner, for example by mixing the active compounds with extenders, that is liquid solvents, liquefied gases under pressure and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide or dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural minerals such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

For combating weeds, the active compounds according to the invention, as such or in the form of their formulations, can also be used as mixtures with known herbicides, finished formulations or tank mixes being possible.

Suitable herbicides for the mixtures are known herbicides, for example anilides such as, for example, diflufenican and propanil; arylcarboxylic acids such as, for example, dichloropicolinic acid, dicamba or picloram; aryloxyalkanoic acids such as, for example, 2,4-D, 2,4-DB, 2,4-DP, fluroxypyr, MCPA, MCPP and triclopyr; aryloxy-phenoxy-alkanoic esters such as, for example, diclofop-methyl, fenoxaprop-ethyl, fluazifop-butyl, haloxyfop-methyl and quizalofop-ethyl; azinones such as, for example, chloridazon and norflurazon; carbamates such as, for example, chlorpropham, desmedipham, phenmedipham and propham; chloroacetanilides such as, for example, alachlor, acetochlor, butachlor, metazachlor, metolachlor, pretilachlor and propachlor; dinitroanilines such as, for example, oryzalin, pendimethalin and trifluralin; diphenyl ethers such as, for example, acifluorfen, bifenox, fluoroglycofen, fomesafen, halosafen, lactofen and oxyfluorfen; ureas such as, for example, chlortoluron, diuron, fluometuron, isoproturon, linuron and methabenzthiazuron; hydroxylamines such as, for example, alloxydim, clethodim, cycloxydim, sethoxydim and tralkoxydim; imidazolinones such as, for example, imazethapyr, imazamethabenz, imazapyr and imazaquin; nitriles such as, for example, bromoxynil, dichlobenil and ioxynil; oxyacetamides such as, for example, mefenacet; sulphonylureas such as, for example, amidosulphuron, bensulphuron-methyl, chlorimuron-ethyl, chlorsulphuron, cinosulphuron, metsulphuron-methyl, nicosulphuron, primisulphuron, pyrazosulphuron-ethyl, thifen-sulphuron-methyl, triasulphuron and tribenuron-methyl; thiocarbamates such as, for example, butylate, cycloate, di-allate, EPTC, esprocarb, molinate, prosulphocarb, thiobencarb and tri-allate; triazines such as, for example, atrazine, cyanazine, simazine, simetryne, terbutryne and terbutylazine; triazinones such as, for example, hexazinone, metamitron and metribuzin; others such as, for example, aminotriazole, benfuresate, bentazone, cinmethylin, clomazone, clopyralid, difenzoquat, dithiopyr, ethofumesate, fluorochloridone, glufosinate, glyphosate, isoxaben, pyridate, quinchlorac, quinmerac, sulphosate and tridiphane.

A mixture with other known active compounds, such as fungicides, insecticides, acaricides, nematicides, bird repellants, plant nutrients and agents which improve soil structure, is also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying; atomising or scattering.

The active compounds according to the invention can be applied either before or after emergence of the plants. They can also be incorporated into the soil before sowing.

The amount of active compound used can vary within a substantial range. It depends essentially on the nature of the desired effect. In general, the amounts used are between 0.001 and 10 kg of active compound per hectare of soil surface, preferably between 0.005 and 5 kg per hectare.

The preparation and use of the active compounds according to the invention can be seen from the following examples.

The preparation and use of the active colapounds according to the invention can be seen from the following examples.

Preparation Examples

EXAMPLE 1

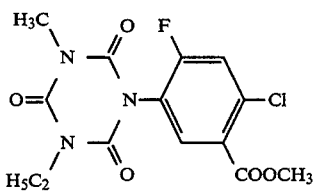

A solution of 1.0 g (0.0028 mol) of 3-(4-chloro-2-fluoro-5-methoxycarbonyl-phenyl)-1-methyl-6-ethoxy-(1H, 3H)-1,3,5-triazine-2,4-dione in 40 ml of toluene is refluxed for 16 hours. For working-up, the solvent is distilled off in vacuo and the residue is dried under a high vacuum.

0.8 g (80% of theory) of 3-(4-chloro-2-fluoro-5-methoxycarbonyl-phenyl)-1-methyl-5-ethyl-1,3,5-triazine-2,4,6-trione of melting point 48°–49° C. is obtained.

EXAMPLE 2

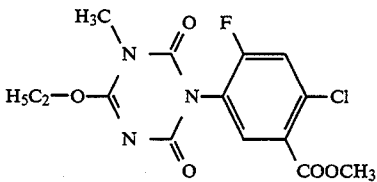

1.3 g (0.009 mol) of potassium carbonate and 1.3 g (0.009 mol) of methyl iodide are added in succession at room temperature to a solution of 2.9 g (0.0085 mol) of 3-(4-chloro-2-fluoro-5-methoxycarbonyl-phenyl)-6-ethoxy-(1H,3H)-1,3,5-triazine-2,4-dione in 100 ml of dry acetonitrile and the mixture is subsequently stirred for 18 hours at room temperature. For working-up, the reaction mixture is poured into water, acidified with hydrochloric acid and extracted using ethyl acetate. The organic phase is dried and the solvent is distilled off in vacuo.

1.3 g (43% of theory) of 3-(4-chloro-2-fluoro-5-methoxycarbonyl-phenyl)-1-methyl-6-ethoxy-(1H,3H)-1,3,5-triazine-2,4-dione of melting point 45°–47° C. are obtained.

EXAMPLE 3

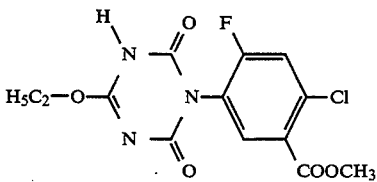

0.7 g (0.002 mol) of sodium methylate is added at room temperature to a solution of 4.5 g (0.012 mol) of N-(4-chloro-2-fluoro-5-methoxycarbonyl-phenyl)-N'-(1-ethoxy-1-methoxycarbonylimino-methyl)-urea in 150 ml of methanol and the mixture is subsequently refluxed for 16 hours. For working-up, the solvent is distilled off in vacuo, the residue is poured into ice-water, and the mixture is acidified with hydrochloric acid. The solid which has precipitated is filtered off with suction, washed with water and dried in vacuo.

2.9 g (71% of theory) of 3-(4-chloro-2-fluoro-5-methoxy-carbonyl-phenyl)-6-ethoxy-(1H,3H)-1,3,5-triazine-2,4-dione of melting point 101°–103° C. are obtained.

EXAMPLE 4

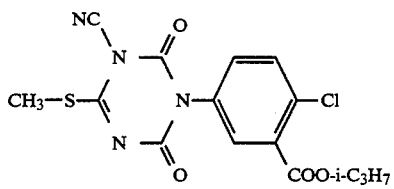

0.8 g (0.008 mol) of triethylamine is added at 0° C. to 5° C. with stirring to a solution of 2.5 g (0.007 mol) of 3-(4-chloro-5-isopropoxycarbonyl-phenyl)-6-methylthio-(1H, 3H)-1,3,5-triazine-2,4-dione and 0.9 g (0.008 mol) of cyanogen bromide in 60 ml of acetone and the mixture is subsequently stirred for 8 to 16 hours at room temperature. For working-up, the reaction mixture is poured into water and extracted using ethyl acetate. The organic phase is separated off, dried and freed from solvent in vacuo.

0.9 g (34% of theory) of 3-(4-chloro-5-isopropoxycarbonyl-phenyl)-1-cyano-6-methylthio-(1H,3H) -1,3,5-triazine-2,4-dione of melting point 55°–56° C. are obtained.

EXAMPLE 5

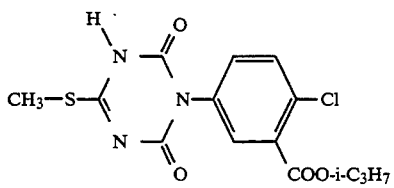

2.7 g (0.05 mol) of sodium methylate are added at room temperature to a solution of 18.2 g (0.047 mol) of N-(4-chloro-3-isopropoxycarbonyl-phenyl)-N'-(1-methylthio-1-methoxycarbonylimino-methyl)-urea in 250 ml of isopropanol and the mixture is subsequently stirred for 16 hours at room temperature. For working-up, the solvent is distilled off in vacuo, the residue is poured into ice-water, and the mixture is acidified with hydrochloric acid and extracted using dichloromethane. The organic phase is washed with dilute hydrochloric acid, dried over magnesium sulphate and concentrated in vacuo. The residue is triturated with methylcyclohexane, filtered off with suction and dried.

9.5 g (57% of theory) of 3-(4-chloro-5-isopropoxycarbonyl-phenyl)-6-methylthio-(1H,3H)-1,3,5-triazine-2,4-dione of melting point 114° C. are obtained.

The following 3-aryl-triazine-2,4-diones of the general formula (I) are obtained in a corresponding manner and following the general preparation instructions:

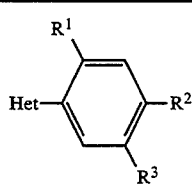

(I)

| Ex. No. | Het | $R^1$ | $R^2$ | $R^3$ | Physical Properties |
|---|---|---|---|---|---|
| 6 | ![Het structure with H3C-N, H3C-S, N] | H | Cl | —COO-i-C$_3$H$_7$ | m.p. 146° C. |
| 7 | ![Het structure with H3C-N, H3C-S, N] | H | Cl | —COO—CH$_3$ | m.p. 183° C. |
| 8 | ![Het structure with H3C-N, H3C-S, N] | F | Cl | —O—CH(CH$_3$)—C≡CH | m.p. 121° C. |

-continued

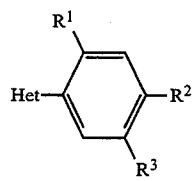
(I)

| Ex. No. | Het | R¹ | R² | R³ | Physical Properties |
|---|---|---|---|---|---|
| 9 | $H_3C$-N, $H_3C$-S on triazinedione | F | Cl | —COO-i-$C_3H_7$ | m.p. 121° C. |
| 10 | $H_3C$-N, $H_3C$-S on triazinedione | F | Cl | —COO—$CH_3$ | m.p. 91–92° C. |
| 11 | $H_3C$-N, $H_5C_2$-S on triazinedione | F | Cl | —COO—$CH_3$ | m.p. 70–72° C. |
| 12 | $H_3C$-N, $H_5C_2$-O on triazinedione | H | Cl | —COO—$CH_3$ | m.p. 155° C. |
| 13 | $H_3C$-N, $H_5C_2$-O on triazinedione | F | Cl | —COO-i-$C_3H_7$ | m.p. 84° C. |
| 14 | $H_3C$-N, $H_5C_2$-O on triazinedione | H | Cl | —COO-i-$C_3H_7$ | m.p. 46–47° C. |
| 15 | $H_3C$-N, $H_3C$-S on triazinedione | F | CN | —O-i-$C_3H_7$ | m.p. 134° C. |

-continued
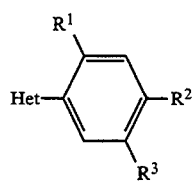
(I)
| Ex. No. | Het | $R^1$ | $R^2$ | $R^3$ | Physical Properties |
|---|---|---|---|---|---|
| 16 | H₃C−N, O=, N−CH₃ (1,3-dimethyl triazinetrione) | H | Cl | −COO-i-C₃H₇ | m.p. 133° C. |
| 17 | H−N, O=, N−CH₃ | H | Cl | −COO-i-C₃H₇ | m.p. 130° C. |
| 18 | H₃C−N, O=, N−CH₃ | F | Cl | −COO-i-C₃H₇ | m.p. 107–109° C. |
| 19 | H₃C−N, O=, N−CH₃ | F | Cl | −COO−CH₃ | m.p. 46–47° C. |
| 20 | NC−N, O=, N−C₂H₅ | F | Cl | −COO−CH₃ | m.p. 185° C. |
| 21 | H−N, H₃C−S−, N | H | Cl | −COO−CH₃ | m.p. 197° C. |
| 22 | H−N, H₃C−O−, N | H | Cl | −COO-i-C₃H₇ | m.p. 175° C. |

-continued
| Ex. No. | Het | R¹ | R² | R³ | Physical Properties |
|---|---|---|---|---|---|
| 23 | H₃C-S, H-N, N, =O, N-, =O (methylthio triazinedione) | F | Cl | —O—CH(CH₃)—C≡CH | ¹H NMR*) 2.62 (s, 3H) |
| 24 | H₃C-S, H-N, N, =O, N-, =O | F | Cl | —COO-i-C₃H₇ | m.p. 185–186° C. |
| 25 | H₃C-O, H-N, N, =O, N-, =O | F | Cl | —COO-i-C₃H₇ | m.p. 201–202° C. |
| 26 | H₃C-S, H-N, N, =O, N-, =O | F | Cl | —COO—CH₃ | m.p. 208–210° C. |
| 27 | H₃C-O, H-N, N, =O, N-, =O | F | Cl | —COO—CH₃ | m.p. 133–135° C. |
| 28 | H₅C₂-O, H₃C-N, N, =O, N-, =O | F | Cl | —O—CH(CH₃)—C≡CH | m.p. 53–55° C. |
| 29 | H₅C₂-S, H-N, N, =O, N-, =O | F | Cl | —COO—CH₃ | m.p. 152° C. |

-continued
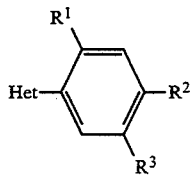
| Ex. No. | Het | R¹ | R² | R³ | Physical Properties |
|---|---|---|---|---|---|
| 30 | H-N, H₅C₂-O-C=N, N(C=O)₂ ring | F | Cl | —COO-i-C₃H₇ | m.p. 60–61° C. |
| 31 | H-N, H₅C₂-O-C=N, N(C=O)₂ ring | H | Cl | —COO-i-C₃H₇ | m.p. 194–195° C. |
| 32 | H-N, H₅C₂-O-C=N, N(C=O)₂ ring | H | Cl | —COO—CH₃ | m.p. 196–107° C. |
| 33 | H-N, H₅C₂-O-C=N, N(C=O)₂ ring | F | Cl | —O—C₂H₅ | m.p. 104–105° C. |
| 34 | H-N, H₅C₂-O-C=N, N(C=O)₂ ring | F | Cl | —O—CH(CH₃)—C≡CH | m.p. 169–170° C. |
| 35 | H-N, H₃C-S-C=N, N(C=O)₂ ring | F | CN | —O-i-C₃H₇ | m.p. 127° C. |
| 36 | H-N, H₅C₂-O-C=N, N(C=O)₂ ring | F | CN | —O-i-C₃H₇ | m.p. 85° C. |

-continued
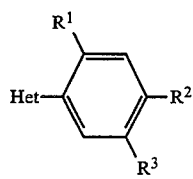
(I)
| Ex. No. | Het | $R^1$ | $R^2$ | $R^3$ | Physical Properties |
|---|---|---|---|---|---|
| 37 | 1,3-dimethyl-ethyl triazinetrione (H3C-N, H5C2-N) | H | Cl | —COO—CH3 | m.p. 65–67° C. |
| 38 | 3-methyl-6-ethoxy (H3C-N, H5C2-O) | F | Cl | —O—C2H5 | m.p. 114–115° C. |
| 39 | 3-methyl-6-methoxy (H3C-N, H3C-O) | H | Cl | —COOCH3 | m.p. 142° C. |
| 40 | 6-methoxy (H-N, H3C-O) | H | Cl | —COOCH3 | m.p. 169° C. |
| 41 | 3-methyl-6-ethoxy (H3C-N, H5C2-O) | F | CN | —O-i-C3H7 | m.p. 87° C. |
| 42 | 1-methyl-3-ethyl triazinetrione (H3C-N, H5C2-N) | H | Cl | —COO-i-C3H7 | m.p. 45° C. |
| 43 | 1-methyl-3-ethyl triazinetrione (H3C-N, H5C2-N) | H | Cl | —COO-i-C3H7 | m.p. 55–56° C. |

-continued

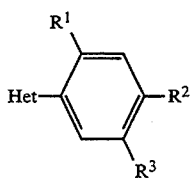
(I)

| Ex. No. | Het | R¹ | R² | R³ | Physical Properties |
|---|---|---|---|---|---|
| 44 | (1,3-dimethyl-triazinetrione; N-Me, N-Et) | F | Cl | —O—C₂H₅ | m.p. 96–97° C. |
| 45 | (H-N, H₃CO-C, triazinedione) | F | Cl | —O—C₂H₅ | m.p. 133° C. |
| 46 | (H₃C-N, H₃CO-C, triazinedione) | F | Cl | —O—C₂H₅ | m.p. 134° C. |
| 47 | (H-N, H₃CO-C, triazinedione) | H | Cl | —O—CH(CH₃)—C≡CH | m.p. 147–148° C. |
| 48 | (H₃C-N, H₃CO-C, triazinedione) | F | Cl | —O—CH(CH₃)—C≡CH | m.p. 45–46° C. |
| 49 | (N,N'-dimethyl triazinetrione) | F | Cl | —O—C₂H₅ | m.p. 139–140° C. |
| 50 | (H-N, H₅C₂O-C, triazinedione) | F | Cl | —S—CH(CH₃)—COOC₂H₅ | m.p. 60–61° C. |

-continued

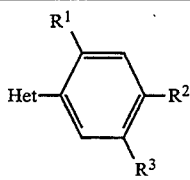

(I)

| Ex. No. | Het | R¹ | R² | R³ | Physical Properties |
|---|---|---|---|---|---|
| 51 | (structure shown) | F | Cl | —S—CH(CH₃)—COOC₂H₅ | ¹H-NMR*): 4,62 (q, 2H) |

Preparation of the starting compounds:

EXAMPLE II-1

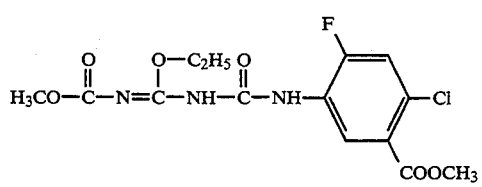

10 g (0.05 mol) of trichloromethyl chloroformate (diphosgene) are added at 70° C. with stirring to a solution of 10.1 g (0.05 mol) of methyl 5-amino-2-chloro-4-fluoro-benzoate in 150 ml of ethyl acetate and the mixture is subsequently refluxed for 2 hours. The solvent is subsequently distilled off, the residue is taken up in 100 ml of dichloromethane, and the mixture is treated with 7.3 g (0.05 mol) of methyl N-(1-ethoxy-1-iminomethyl)-carbamate and stirred for 12 to 16 hours at room temperature. For working-up, precipitate which has separated out is filtered off with suction, the filtrate is concentrated in vacuo, and the residue is recrystallised from isopropanol.

5.3 g (28% of theory) of N-(4-chloro-2-fluoro-5-methoxycarbonyl-phenyl)-N'-(1-ethoxy-1-methoxycarbonyliminomethyl)-urea of melting point 105°–107° C. are obtained.

EXAMPLE II-2

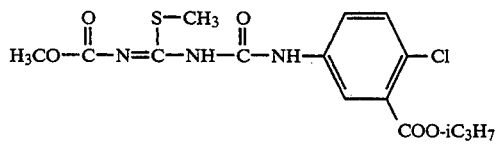

12 g (0.06 mol) of trichloromethyl chloroformate (diphosgene) are added at 70° C. with stirring to a solution of 12.9 g (0.06 mol) of isopropyl 5-amino-2-chlorobenzoate in 200 ml of ethyl acetate and the mixture is subsequently refluxed for 2 hours. The solvent is subsequently distilled off, the residue is taken up in 100 ml of dichloromethane, and the mixture is treated with 8.9 g (0.06 mol) of methyl N-(1-methylthio-1-iminomethyl)-carbamate and stirred for 16 hours at room temperature. For working-up, the solvent is distilled off in vacuo, and the residue which remains is triturated with methylcyclohexane, filtered off with suction and dried.

22.6 g (97% of theory) of N-(4-chloro-5-isopropoxycarbonyl-phenyl)-N'-(1-methylthio-1-methoxycarbonyliminomethyl)-urea of melting point 93°–94° C. are obtained.

The following substituted phenylurea derivatives of the general formula (II) are obtained in a corresponding manner and following the general preparation instructions:

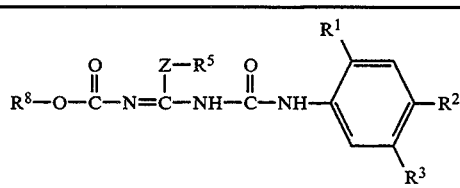

(II)

| Ex. No. | R¹ | R² | R³ | R⁵ | R⁸ | Z | Melting Point/°C. |
|---|---|---|---|---|---|---|---|
| II-3 | H | Cl | —COO—CH₃ | CH₃ | CH₃ | S | 158 |
| II-4 | H | Cl | —COO-i-C₃H₇ | CH₃ | CH₃ | O | 108 |
| II-5 | F | Cl | —COO-i-C₃H₇ | CH₃ | CH₃ | S | 129–131 |
| II-6 | F | Cl | —COO-i-C₃H₇ | CH₃ | CH₃ | O | 100–101 |
| II-7 | F | Cl | —COO—CH₃ | CH₃ | CH₃ | S | 167–169 |
| II-8 | F | Cl | —COO—CH₃ | CH₃ | CH₃ | O | 159–160 |
| II-9 | F | Cl | —COO—CH₃ | C₂H₅ | CH₃ | S | 115–116 |
| II-10 | H | Cl | —COO-i-C₃H₇ | C₂H₅ | CH₃ | O | 110–111 |
| II-11 | H | Cl | —COO—CH₃ | C₂H₅ | CH₃ | O | 106–107 |
| II-12 | F | Cl | —COO-i-C₃H₇ | C₂H₅ | CH₃ | O | 75–76 |
| II-13 | F | Cl | —O—CH(CH₃)—C≡CH | C₂H₅ | CH₃ | O | 81–82 |
| II-14 | F | Cl | —O—C₂H₅ | C₂H₅ | CH₃ | O | 75–77 |

-continued

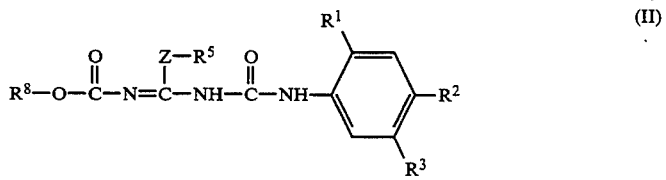

| Ex. No. | R¹ | R² | R³ | R⁵ | R⁸ | Z | Melting Point/°C |
|---------|----|----|----|----|----|----|------------------|
| II-15 | F | CN | —O-i-C₃H₇ | CH₃ | CH₃ | S | 129 |
| II-16 | F | CN | —O-i-C₃H₇ | C₂H₅ | CH₃ | O | 122–123 |
| II-17 | F | Cl | —O—CH(CH₃)—C≡CH | CH₃ | CH₃ | S | |
| II-18 | F | Cl | —O—C₂H₅ | CH₃ | CH₃ | O | 92–94 |
| II-19 | F | Cl | —O—CH(CH₃)C≡CH | CH₃ | CH₃ | O | 74–75 |
| II-20 | F | Cl | —S—CH(CH₃)—COOC₂H₅ | C₂H₅ | CH₃ | O | Oil |

Use Examples

In the use examples which follow, the compound indicated below was employed as comparison substance:

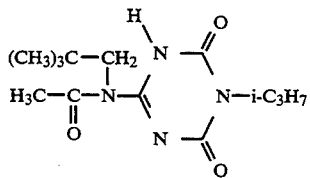

(A)

3-Isopropyl-6-[N-acetyl-N-(2,2-dimethyl-1-propyl)-amino]-(3H,5H)-1,3,5-triazine-2,4-dione (cf., for example, DE 2,603,180)

EXAMPLE A

Pre-emergence test

Solvent: 5 parts by weight of acetone

Emulsifier: 1 part by weight of alkylaryl polyglycol ether

To produce a suitable preparation of active compound, one part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0% = no action (like untreated control)

100% = total destruction

In this test, a clearly superior activity compared with the prior art in terms of activity as well as crop plant selectivity is shown, for example, by the compound of Preparation Examples 7.

EXAMPLE B

Post-emergence test

Solvent: 5 parts by weight of acetone

Emulsifier: 1 part by weight of alkylaryl polyglycol ether

To produce a suitable preparation of active compound, one part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. After three weeks, the degree of damage to the plants is rated in % damage in comparison to the development of the untreated control.

The figures denote:

0% = no action (like untreated control)

100% = total destruction

In this test, a clearly superior activity compared with the prior art in terms of activity as well as crop plant selectivity is shown, for example, by the compound of Preparation Examples 6.

EXAMPLE C

Defoliation and desiccation of the leaves of cotton

Solvent: 30 parts by weight of dimethyformamide

Emulsifier: 1 part by weight of polyoxyethylene sorbitan monolaureat

To produce a suitable preparation of active compound, one part by weight of active compound is mixed with the stated amounts of solvent and emulsifier and the concentrate is made up to the desired concentration with water.

Cotton plants are grown in the greenhouse until the fifth subsequent leaf has unfolded completely. In this stage, the plants are sprayed with the preparations of active compound until dripping wet. After one week, the shedding of leaves and the desiccation of the leaves are rated in comparison with the development of the untreated control.

In this test, a clearly superior activity compared with the untreated control is shown, for example, by the compound of Preparation Example 6.

It will be understood that the specification and examples are illustrative but not limitative of the present invention and that other embodiments within the spirit and scope of the invention will suggest themselves to those skilled in the art.

What is claimed is:

1. A 3-aryl-triazine-2,4-dione of the formula,

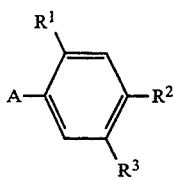 (I)

wherein

A represents a radical of the formula

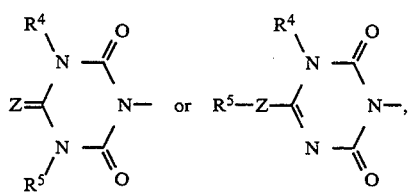

wherein
- $R^1$ represents hydrogen or halogen,
- $R^2$ represents halogen, cyano or nitro and
- $R^3$ represents a radical of the formula —CO—X—$R^7$, in which
- $R^4$ represents hydrogen, cyano, alkyl, alkenyl, alkynyl or halogenoalkyl,
- $R^5$ represents alkyl, alkenyl or alkynyl,
- $R^7$ represents hydrogen or optionally substituted alkyl,
- X represents oxygen or sulphur and
- Z represents oxygen or sulphur.

2. A 3-aryl-triazine-2,4-dione according to claim 1, wherein

A represents a radical of the formula

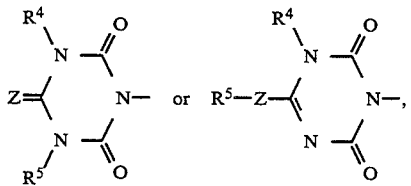

wherein
- $R^1$ represents hydrogen, fluorine, chlorine, bromine or iodine,
- $R^2$ represents fluorine, chlorine, bromine, iodine, cyano or nitro,
- $R^3$ represents a radical of the formula —CO—X—$R^7$ in which
- $R^4$ represents hydrogen, cyano, straight-chain or branched alkyl having 1 to 8 carbon atoms, straight-chain or branched alkenyl having 2 to 8 carbon atoms, straight-chain or branched alkynyl having 2 to 8 carbon atoms or straight chain or branched halogenoalkyl having 1 to 6 carbon atoms and 1 to 13 identical or different halogen atoms,
- $R^5$ represents straight-chain or branched alkyl having 1 to 8 carbon atoms, straight-chain or branched alkenyl having 2 to 8 carbon atoms or straight-chain or branched alkynyl having 2 to 8 carbon atoms,
- $R^7$ represents hydrogen, straight-chain or branched alkyl having 1 to 8, carbon atoms, straight-chain or branched halogenoalkyl having 1 to 6 carbon atoms and 1 to 13 identical or different halogen atoms, in each case straight-chain or branched alkoxyalkyl, alkoxycarbonylalkyl, alkylcarbonyloxyalkyl, alkylthiocarbonylalkyl or alkylcarbonylthioalkyl, each of which has 1 to 6 carbon atoms in the individual alkyl moieties or represents arylalkyl which has 6 or 10 carbon atoms in the aryl moiety and 1 to 6 carbon atoms in the straight-chain or branched alkyl moiety wherein aryl moiety is optionally monosubstituted or polysubstituted by identical or different substituents, wherein the substituents on the aryl moiety are halogen, cyano, nitro, in each case straight-chain or branched alkyl, alkoxy, alkylthio, alkylsulphinyl or alkylsulphonyl, each of which has 1 to 4 carbon atoms, in each case straight-chain or branched halogenoalkyl, halogenoalkoxy, halogenoalkylthio, halogenoalkylsulphinyl or halogenoalkylsulphonyl, each of which has 1 to 4 carbon atoms and 1 to 9 identical or different halogen atoms, in each case straight-chain or branched alkoxycarbonyl or alkoximinoalkyl, each of which has 1 to 4 carbon atoms in the individual alkyl moieties and phenyl which is optionally monosubstituted or polysubstituted by identical or different substituents selected from the group consisting of halogen, straight-chain or branched alkyl, straight-chain or branched alkoxy, straight-chain or branched halogenoalkyl, and straight-chain or branched halogenoalkoxy, each of which has 1 to 4 carbon atoms and 1 to 9 identical or different halogen atoms,

- X represents oxygen or sulphur and
- Z represents oxygen or sulphur.

3. A 3-aryl-triazine-2,4-dione according to claim 1, wherein

A represents a radical of the formula

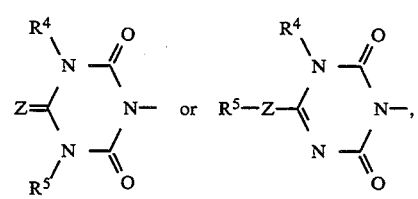

wherein
- $R^1$ represents hydrogen, fluorine, chlorine or bromine,
- $R^2$ represents fluorine, chlorine, bromine, cyano or nitro,
- $R^3$ represents a radical of the formula —CO—X—$R^7$, in which
- $R^4$ represents hydrogen, cyano, straight-chain or branched alkyl having 1 to 6 carbon atoms, straight-chain or branched alkenyl having 2 to 6 carbon atoms, straight-chain or branched alkynyl having 2 to 6 carbon atoms or straight-chain or branched halogenoalkyl having 1 to 4 carbon atoms and 1 to 9 identical or different halogen atoms,
- $R^5$ represents straight-chain or branched alkyl having 1 to 6 carbon atoms, straight-chain or branched alkenyl having 2 to 6 carbon atoms or straight-chain or branched alkynyl having 2 to 6 carbon atoms, R⁷ represents hydrogen, straight-chain or branched alkyl having 1 to 6 carbon atoms, straight-chain or branched halogenoalkyl having 1 to 4 carbon atoms and 1 to 9 identical or different halogen atoms, or represents in each case straight-chain or branched alkoxyalkyl, alkoxycarbonylalkyl, alkylcarbonyloxyalkyl, alkylthiocarbonylalkyl or alkylcarbonylthioalkyl, each of which has 1 to 4 carbon atoms in the individual alkyl moieties, or represents phenylalkyl which has 1 to 4 carbon atoms in the straight-chain or branched alkyl moiety wherein phenyl moiety is optionally monosubstituted to pentasubstituted by identical or different substituents, wherein the substituents on the phenyl moiety are halogen, cyano, nitro, in each case straight-chain or branched alkyl, alkoxy, alkylthio, alkylsulphinyl or alkylsulphonyl, each of which has 1 to 3 carbon atoms, in each case straight-chain or branched halogenoalkyl, halogenoalkoxy, halogenoalkylthio, halogenoalkylsulphinyl or halogenoalkylsulphonyl, each of which has 1 to 3 carbon atoms and 1 to 7 identical or different halogen atoms, in each case straight-chain or branched alkoxycarbonyl or alkoximinoalkyl, each of which has 1 to 3 carbon atoms in the individual alkyl moieties and phenyl which is optionally monosubstituted or polysubstituted by identical or different substituents selected from the group consisting of halogen, straight-chain or branched alkyl, straight-chain or branched alkoxy, straight-chain or branched halogenoalkyl, and straight-chain or branched halogenoalkoxy, each of which has 1 to 3 carbon atoms and 1 to 7 identical or different halogen atoms, X represents oxygen or sulphur and
Z represents oxygen or sulphur.

4. A 3-aryl-triazine-2,4-dione according to claim 1, wherein
A represents a radical of the formula

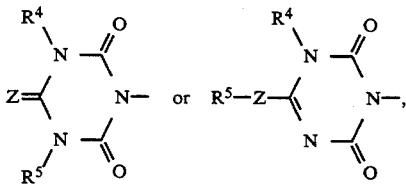

wherein
R¹ represents hydrogen, fluorine or chlorine,
R² represents fluorine, chlorine, cyano or nitro,
R³ represents a radical of the formula —CO—X—R⁷, in which
R⁴ represents hydrogen, cyano, straight-chain or branched alkyl having 1 to 4 carbon atoms, straight-chain or branched alkenyl having 2 to 4 carbon atoms, straight-chain or branched alkynyl having 2 to 4 carbon atoms or straight-chain or branched halogenoalkyl having 1 to 3 carbon atoms and 1 to 7 identical or different halogen atoms,
R⁵ represents straight-chain or branched alkyl having 1 to 4 carbon atoms, straight-chain or branched alkenyl having 2 to 4 carbon atoms or straight-chain or branched alkynyl having 2 to 4 carbon atoms,
R⁷ represents hydrogen, straight-chain or branched alkyl having 1 to 4 carbon atoms, straight-chain or branched halogenoalkyl having 1 to 3 carbon atoms and 1 to 7 identical or different halogen atoms, or represents in each case straight-chain or branched alkoxyalkyl, alkoxycarbonylalkyl, alkylcarbonyloxyalkyl, alkylthiocarbonylalkyl or alkylcarbonylthioalkyl, each of which has 1 to 3 carbon atoms in the individual alkyl moieties, or represents phenylalkyl which has 1 to 2 carbon atoms in the alkyl moiety wherein phenyl moiety is optionally monosubstituted to trisubstituted by identical or different substituents, wherein the substituents on the phenyl ring are fluorine, chlorine, bromine, cyano, nitro, methyl, ethyl, n-or i-propyl, n-, i-, s- or t-butyl, methoxy, ethoxy, n- or i-propoxy, n-, i-, s-or t-butoxy, methylthio, ethylthio, methylsulphinyl, ethylsulphinyl, methylsulphonyl, ethylsulphonyl, trifluoromethyl, difluoromethyl, trifluoromethoxy, difluoromethoxy, trifluoromethylthio, trifluoromethylsulphinyl, trifluoromethylsulphonyl, methoxycarbonyl, ethoxycarbonyl, methoximinomethyl, methoximinoethyl, ethoximinomethyl, ethoximinoethyl and phenyl which is optionally monosubstituted to trisubstituted by identical or different substituents selected from the group consisting of fluorine, chlorine, bromine, methyl, ethyl, n-propyl, i-propyl, methoxy, ethoxy, trifluoromethyl and trifluoromethoxY, X represents oxygen or sulphur and
Z represents oxygen or sulphur.

5. A 3-aryl-triazine-2,4-dione according to claim 1 wherein such compound is 3-(4-chloro-5-isopropoxycarbonyl-phenyl)-1-methyl-6-methylthio-(1H, 3H)-1,3,5-triazine-2,4-dione of the formula

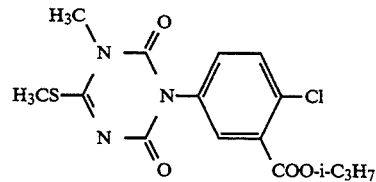

6. A 3-aryl-triazine-2,4-dione according to claim 1 wherein such compound is 3-(4-chloro-5-methoxycarbonylphenyl)-1-methyl-6-methylthio-(1H, 3H)-1,3,5-triazine-2,4-dione of the formula

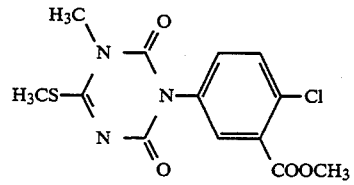

7. A herbicidal composition comprising a herbicidally effective amount of a compound according to claim 1 and a diluent.

8. A method of combating unwanted vegetation which comprises applying to such vegetation or to a locus from which it is desired to exclude such vegetation a herbicidally effective amount of a compound according to claim 1.

9. The method according to claim 8, wherein such compound is
3-(4-chloro-5-isopropoxycarbonyl-phenyl)-1-methyl-6-methylthio-(1H, 3H)-1,3,5-triazine-2,4-dione, and
3-(4-chloro-5-methoxycarbonyl-phenyl)-1-methyl-6-methylthio-(1H, 3H)-1,3,5-triazine-2,4-dione.

* * * * *